(12) United States Patent
Tanigami et al.

(10) Patent No.: US 10,939,935 B2
(45) Date of Patent: Mar. 9, 2021

(54) ULTRASONIC TREATMENT INSTRUMENT FOR ARTICULATIONS, AND ULTRASONIC TREATMENT SYSTEM FOR ARTICULATIONS

(71) Applicant: OLYMPUS CORPORATION, Hachioji (JP)

(72) Inventors: Yasuo Tanigami, Hachioji (JP); Koichiro Watanabe, Higashiyamato (JP); Norihiro Yamada, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 224 days.

(21) Appl. No.: 16/116,617

(22) Filed: Aug. 29, 2018

(65) Prior Publication Data

US 2018/0368878 A1    Dec. 27, 2018

Related U.S. Application Data

(63) Continuation of application No. PCT/JP2016/056102, filed on Feb. 29, 2016.

(51) Int. Cl.
*A61B 17/32* (2006.01)
*A61B 17/16* (2006.01)
*A61B 17/00* (2006.01)

(52) U.S. Cl.
CPC ...... *A61B 17/320068* (2013.01); *A61B 17/16* (2013.01); *A61B 17/1626* (2013.01);
(Continued)

(58) Field of Classification Search
CPC .............. A61B 17/32; A61B 17/3205; A61B 17/320068
See application file for complete search history.

(56) References Cited

U.S. PATENT DOCUMENTS

| | | | | |
|---|---|---|---|---|
| 5,628,743 A | * | 5/1997 | Cimino | A61B 17/320068 606/1 |
| 2006/0229624 A1 | * | 10/2006 | May | A61B 17/32002 606/79 |
| 2008/0234709 A1 | * | 9/2008 | Houser | A61B 17/320068 606/169 |

(Continued)

FOREIGN PATENT DOCUMENTS

| | | |
|---|---|---|
| CN | 101674779 A | 3/2010 |
| JP | S59-186547 A | 10/1984 |

(Continued)

OTHER PUBLICATIONS

May 24, 2016 International Search Report issued in International Patent Application PCT/JP2016/056102.

(Continued)

*Primary Examiner* — Christopher J Beccia
(74) *Attorney, Agent, or Firm* — Oliff PLC

(57) ABSTRACT

An ultrasonic treatment instrument for articulations has a bone abrasion mode in which vibration is performed at a first frequency and a first amplitude, and a cartilage dissolution mode in which vibration is performed at a second frequency which is higher than the first frequency, and a second amplitude which is less than the first amplitude, wherein a first vibration velocity, which is a product of the first frequency and the first amplitude, and a second vibration velocity, which is a product of the second frequency and the second amplitude, coincide or substantially coincide.

15 Claims, 4 Drawing Sheets

(52) U.S. Cl.
CPC ............... *A61B 2017/00146* (2013.01); *A61B 2017/00176* (2013.01); *A61B 2017/320004* (2013.01); *A61B 2017/320071* (2017.08); *A61B 2017/320089* (2017.08)

(56) References Cited

U.S. PATENT DOCUMENTS

| | | | | |
|---|---|---|---|---|
| 2013/0030328 | A1* | 1/2013 | Dycus | A61B 17/320092 |
| | | | | 601/2 |
| 2013/0035679 | A1* | 2/2013 | Orszulak | A61B 18/1233 |
| | | | | 606/33 |
| 2015/0142033 | A1 | 5/2015 | Stulen et al. | |
| 2015/0272657 | A1* | 10/2015 | Yates | A61B 18/1206 |
| | | | | 606/34 |

FOREIGN PATENT DOCUMENTS

| | | |
|---|---|---|
| JP | H11-503061 A | 3/1999 |
| JP | 2001-170066 A | 6/2001 |
| JP | 2003-116870 A | 4/2003 |
| JP | 2010-522030 A | 7/2010 |
| JP | 2015-43879 A | 3/2015 |
| JP | 2015-128628 A | 7/2015 |

OTHER PUBLICATIONS

Jun. 25, 2019 Office Action issued in Japanese Patent Application No. 2018-502876.
Jun. 3, 2020 Office Action issued in Chinese Patent Application No. 201680082860.1.

* cited by examiner

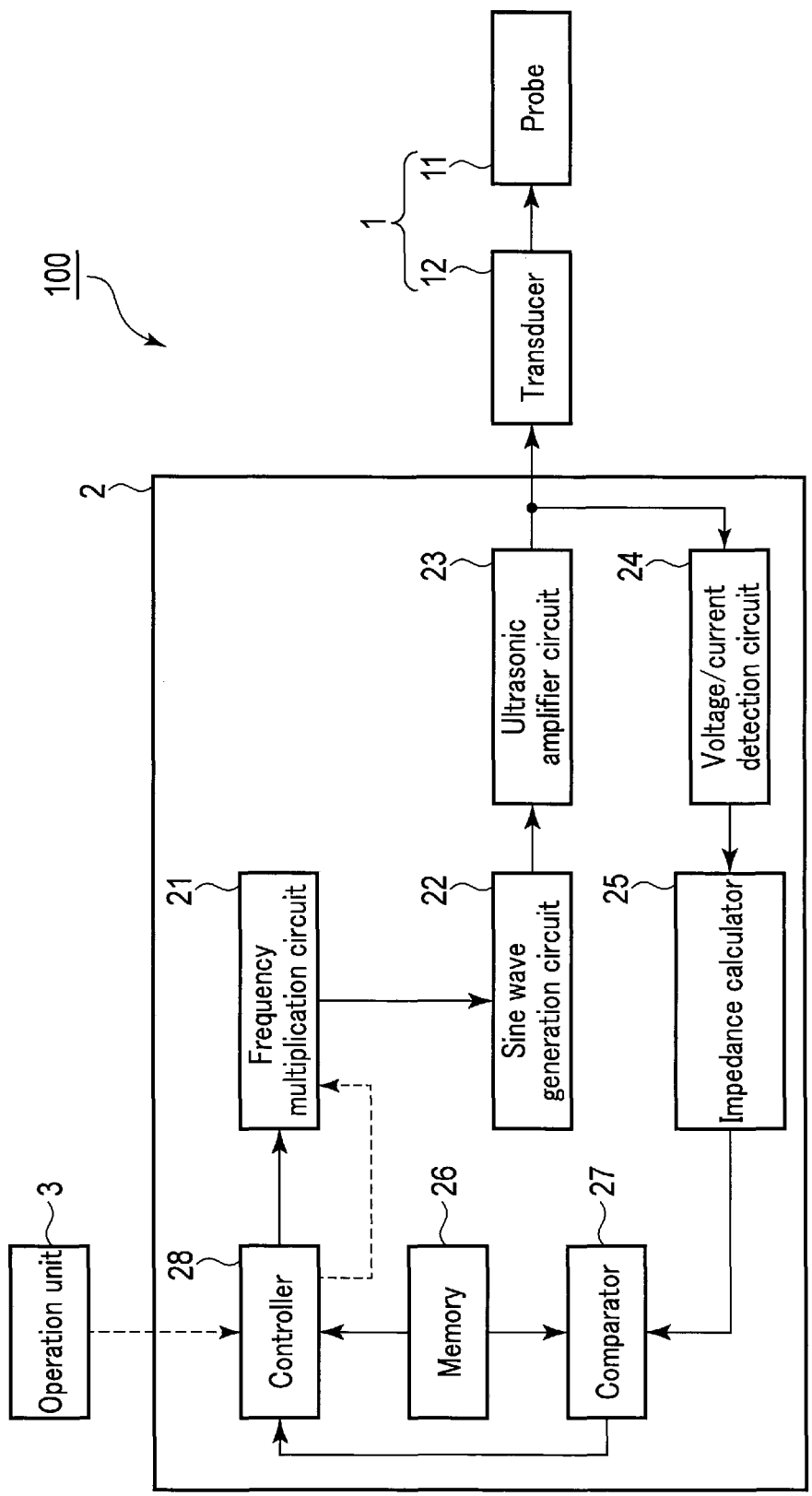
F I G. 1

|  | Increase rate of first outside-diameter variation portion | Increase rate of second outside-diameter variation portion | Total increase rate |
|---|---|---|---|
| Basic mode | Substantially 1 time | 5.83 times | Substantially 5.83 times |
| Triple higher-order mode | 1.79 times | 3.25 times | 5.83 times |
| Basic mode/ triple higher-order mode | — | 1.79 | — |

F I G. 3

ULTRASONIC TREATMENT INSTRUMENT FOR ARTICULATIONS, AND ULTRASONIC TREATMENT SYSTEM FOR ARTICULATIONS

CROSS-REFERENCE TO RELATED APPLICATIONS

This application is a Continuation Application of PCT Application No. PCT/JP2016/056102, filed Feb. 29, 2016, the entire contents of which are incorporated herein by reference.

BACKGROUND OF THE INVENTION

1. Field of the Invention

The present invention relates to an ultrasonic treatment instrument for articulations, and an ultrasonic treatment system for articulations.

2. Description of the Related Art

As an ultrasonic treatment instrument, there is known an ultrasonic treatment instrument which can abrade a bone or cartilage, for example, as disclosed in Jpn. Pat. Appln. KOKAI Publication No. 2003-116870. Such an ultrasonic treatment instrument has both a function of abrasion by mechanical vibration (hereinafter referred to as "hammering effect") and a function of abrasion (dissolution) by frictional heat on a tissue.

In recent years, the use of the ultrasonic treatment instrument for treating articulations has been studied. An articulation includes a cartilage, and a bone composed of a cortical bone and a cancellous bone. The ultrasonic treatment instrument is used not only for treating the cartilage, but also for treating the cortical bone and cancellous bone.

It has become clearer that the resection mechanism of a cartilage and the abrasion mechanism of a cortical bone and a cancellous bone are different due to a difference in nature between the cartilage and the cortical bone and cancellous bone. It is thought that the resection mechanism of the cartilage is frictional heat between the treatment instrument and cartilage by ultrasonic vibration. On the other hand, it is thought that the abrasion mechanism of the cortical bone and cancellous bone is the hammering effect on the cortical bone and cancellous bone by the treatment instrument to which ultrasonic vibration is transmitted. As described above, the ultrasonic treatment instrument has both the function of abrasion by the hammering effect and the function of abrasion by the frictional heat. Thus, even when a surgeon tries to abrade only the cartilage by the ultrasonic treatment instrument, it can be thought that the hammering effect of the ultrasonic treatment instrument acts on the cortical bone and cancellous bone near the cartilage.

BRIEF SUMMARY OF THE INVENTION

An ultrasonic treatment instrument for articulations according to an embodiment of the present invention has a bone abrasion mode in which vibration is performed at a first frequency and a first amplitude, and a cartilage dissolution mode in which vibration is performed at a second frequency which is higher than the first frequency, and a second amplitude which is less than the first amplitude, wherein a first vibration velocity, which is a product of the first frequency and the first amplitude, and a second vibration velocity, which is a product of the second frequency and the second amplitude, coincide or substantially coincide.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram of an ultrasonic treatment system for articulations according to an embodiment.

FIG. 3 is a table illustrating increase rates of vibration velocity in the ultrasonic treatment instrument for articulations according to an embodiment.

DETAILED DESCRIPTION OF THE INVENTION

Figure 2:
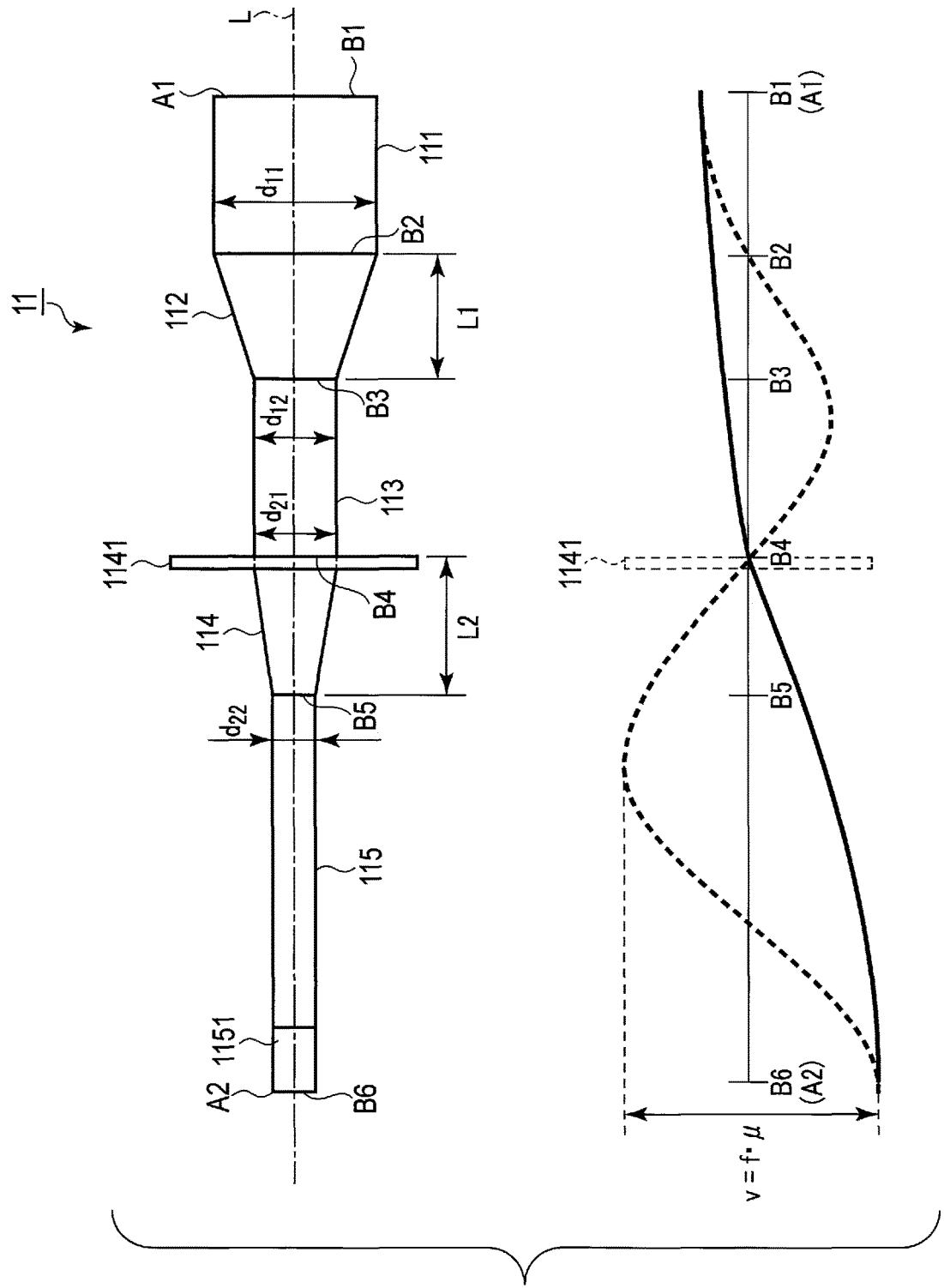
FIG. 2 is a schematic view illustrating an ultrasonic treatment instrument for articulations according to an embodiment.

Hereinafter, an embodiment for implementing the present invention will be described with reference to the accompanying drawings.

An ultrasonic treatment system for articulations (hereinafter referred to as "treatment system") is described.

FIG. 1 is a block diagram of a treatment system 100.

The treatment system 100 includes an ultrasonic treatment instrument for articulations (hereinafter referred to as "treatment instrument") 1, a control unit 2 and an operation unit 3.

The treatment instrument 1 includes a probe 11 and a transducer 12.

The probe 11 is an example of a vibration transmission member which transmits ultrasonic vibration. By the transmission of ultrasonic vibration, the probe 11 abrades, by a treatment section 1151 (to be described later) provided at a distal end of the probe 11, a cartilage, or a bone composed of a cortical bone and a cancellous bone, which is a treated target in an articulation. The components of the cartilage and the components of the cortical bone and cancellous bone are different. The cartilage has a large content of collagen, and it is understood that the cartilage melts, for example, at about 60° C. to 70° C. On the other hand, the cortical bone and cancellous bone have a large content of lime components such as calcium and phosphoric acid, and is thus harder than the cartilage. In addition, it is known that the melting points of the cortical bone and cancellous bone exceed several hundred degrees centigrade. Hereinafter, the cortical bone will be described as a representative of the cortical bone and cancellous bone. However, it is assumed that the term "cortical bone" can be read, as needed, as "at least one of the cortical bone and cancellous bone".

As will be described later, the probe 11 is configured such that frictional heat energy $W_\mu$ at the distal end of the probe 11 coincides, regardless of the frequencies of ultrasonic vibration. Note that the term "coincide" used in the present embodiment is intended to mean "coincide or substantially coincide".

The frictional heat energy $W_\mu$ will be described.

The frictional heat energy $W_\mu$ is expressed by the following equation (1).

$$W_\mu = \int_0^{2\pi} Fv dt \cdot ft = 4\mu N \cdot fu_0 \cdot t \qquad \text{equation (1)}$$

Here, $\mu$ is a statical friction coefficient; N is a vertical drag; $\mu$N, which is a product of the statical friction coefficient and vertical drag, is frictional force; f is a frequency of ultrasonic vibration which is transmitted in the probe 11; $u_0$ is an amplitude at the distal end of the probe 11; $fu_0$, which is a product of the frequency and amplitude, is vibration velocity at the distal end of the probe 11; and t is time.

According to equation (1), the frictional heat energy $W_\mu$ is proportional to the vibration velocity.

The transducer 12 is an example of an ultrasonic vibration generator. The transducer 12 is, for example, a bolt-clamped Langevin-type transducer (BLT). The transducer 12 is connected to the probe 11. The transducer 12 vibrates (longitudinally vibrates) along a longitudinal axis L of the probe 11 (to be described later) in accordance with a driving signal which is supplied from the control unit 2, and generates ultrasonic vibration. The transducer 12 transmits the ultrasonic vibration to the probe 11.

The transducer 12 transmits different ultrasonic vibrations to the probe 11 between a first mode and a second mode.

The first mode is a bone abrasion mode for treating a cortical bone or a cancellous bone. The first mode is a mode in which the probe 11 transmits ultrasonic vibration of a characteristic resonance frequency of a basic mode (also referred to as "primary mode") in the treatment instrument 1. The characteristic resonance frequency of the basic mode is referred to as "first frequency". The ultrasonic vibration of the first frequency is referred to as "first ultrasonic vibration".

In the first mode, the transducer 12 vibrates at the first frequency, and generates the first ultrasonic vibration. The transducer 12 transmits the first ultrasonic vibration to the probe 11.

The second mode is a cartilage dissolution mode for treating a cartilage. The second mode is a mode in which the probe 11 transmits ultrasonic vibration of a frequency of a higher-order mode in the treatment instrument 1, and makes the amplitude at the distal end of the probe 11 less than in the first mode. The frequency of the higher-order mode is a frequency which is n-times higher than the first frequency. The frequency, which is n-times higher than the first frequency, is referred to as "second frequency". The ultrasonic vibration of the second frequency is referred to as "second ultrasonic vibration".

Here, n is an integer of 2 or more. The frequency of the higher-order mode is, preferably, an odd-number of times of the first frequency. In the second mode, the number of times per second of the contact of the treatment section 1151 with a tissue is greater than in the first mode.

In the second mode, the transducer 12 vibrates at the second frequency, and generates the second ultrasonic vibration. The transducer 12 transmits the second ultrasonic vibration to the probe 11.

The control unit 2 supplies different driving signals to the transducer 12 between the first mode and second mode. In the first mode, the control unit 2 supplies a first driving signal to the transducer 12. The frequency of the first driving signal is the first frequency. In the second mode, the control unit 2 supplies a second driving signal to the transducer 12. The second driving signal has the same amplitude as the first driving signal, and has the second frequency. The transducer 12 is driven with an equal predetermined electric power in each operation mode of the first mode and second mode.

The control unit 2 includes a frequency multiplication circuit 21, a sine wave generation circuit 22, an ultrasonic amplifier circuit 23, a voltage/current detection circuit 24, an impedance calculator 25, a memory 26, a comparator 27 and a controller 28.

The frequency multiplication circuit 21 executes different processes in accordance with an operation instruction in the first mode or an operation instruction in the second mode from the controller 28.

In the first mode, the frequency multiplication circuit 21 stops a process of multiplying the frequency of the signal of the first frequency, which is supplied from the controller 28. The frequency multiplication circuit 21 supplies the signal of the first frequency to the sine wave generation circuit 22.

In the second mode, the frequency multiplication circuit 21 multiplies the frequency of the signal of the first frequency, which is supplied from the controller 28. The frequency multiplication circuit 21 supplies a signal of the second frequency, which is equal to an n-times the first frequency, to the sine wave generation circuit 22.

The sine wave generation circuit 22 generates a driving signal of a sine wave for driving the transducer 12.

In the first mode, the sine wave generation circuit 22 generates the above-described first driving signal. The sine wave generation circuit 22 supplies the first driving signal to the ultrasonic amplifier circuit 23.

In the second mode, the sine wave generation circuit 22 generates the above-described second driving signal. The sine wave generation circuit 22 supplies the second driving signal to the ultrasonic amplifier circuit 23.

The ultrasonic amplifier circuit 23 amplifies the first driving signal or second driving signal, which is supplied from the sine wave generation circuit 22. The ultrasonic amplifier circuit 23 supplies the amplified first driving signal or the amplified second driving signal to the transducer 12.

The voltage/current detection circuit 24 detects the value of output voltage (the amplitude of a voltage waveform), the value of output current (the amplitude of a current waveform) and a voltage-current phase between voltage and current, by referring to the first driving signal or second driving signal which the ultrasonic amplifier circuit 23 supplies to the transducer 12. The voltage/current detection circuit 24 supplies the value of output voltage, the value of output current and the voltage-current phase to the impedance calculator 25.

The impedance calculator 25 calculates an impedance (|Z|), based on the value of output voltage, the value of output current and the voltage-current phase. The impedance calculator 25 sends the impedance (|Z|) to the comparator 27.

The memory 26 stores various kinds of information.

In one example, the memory 26 stores a threshold for cortical bone treatment and a threshold for cartilage treatment.

The threshold for cortical bone treatment is set for detecting that the treatment section 1151 is in contact with the cortical bone. The threshold for cortical bone treatment is based on a value of the sum of the impedance of the treatment instrument 1 itself, and an impedance due to the cortical bone which is a treated target.

The threshold for cartilage treatment is set for detecting that the treatment section 1151 is in contact with the cartilage. The threshold for cartilage treatment is based on a value of the sum of the impedance of the treatment instrument 1 itself, and an impedance due to the cartilage which is a treated target.

The threshold for cortical bone treatment and the threshold for cartilage treatment are exclusively set.

In another example, the memory 26 stores an operation program of the first mode. The memory 26 stores an operation program of the second mode.

The comparator 27 compares the impedance value from the impedance calculator 25 with the threshold for cortical bone treatment and the threshold for cartilage treatment, which are stored in the memory 26. The comparator 27 sends a comparison result to the controller 28.

The controller 28 controls the respective components in the control unit 2.

In one example, the controller 28 sets the operation mode to the first mode or second mode, as described below.

The controller 28 detects whether the treatment section 1151 is in contact with either the cartilage or the cortical bone, by referring to the comparison result from the comparator 27.

If the controller 28 detects that the treatment section 1151 is in contact with the cortical bone, the controller 28 sets the operation mode to the first mode. When the current operation mode is the first mode, the controller 28 keeps the operation mode as the first mode. When the current operation mode is the second mode, the controller 28 changes the operation mode from the second mode to the first mode. Specifically, the controller 28 sends an operation instruction in the first mode to the frequency multiplication circuit 21.

If the controller 28 detects that the treatment section 1151 is in contact with the cartilage, the controller 28 sets the operation mode to the second mode. When the current operation mode is the second mode, the controller 28 keeps the operation mode as the second mode. When the current operation mode is the first mode, the controller 28 changes the operation mode from the first mode to the second mode. Specifically, the controller 28 sends an operation instruction in the second mode to the frequency multiplication circuit 21.

The operation unit 3 accepts setting for the control unit 2. The operation unit 3 is, for example, a switch.

In one example, the operation unit 3 accepts a change of the operation mode. Based on the change of the operation mode, the controller 28 refers to the operation program in the memory 26 and sends an operation instruction in the first mode or second mode to the frequency multiplication circuit 21.

In another example, the operation unit 3 accepts a change of the number of multiplication in the frequency multiplication circuit 21. Based on the change of the number of multiplication in the operation unit 3, the controller 28 sends an instruction to change the number of multiplication in the frequency multiplication circuit 21 to the frequency multiplication circuit 21. Based on the instruction from the controller 28, the frequency multiplication circuit 21 changes the number of multiplication.

The above-mentioned probe 11 will be described.

An upper part of FIG. 2 is a schematic view illustrating an example of the probe 11. A lower part of FIG. 2 is a schematic view illustrating vibration velocity (solid line) of the first ultrasonic vibration and vibration velocity (broken line) of the second ultrasonic vibration, which are transmitted in the probe 11. In FIG. 2, it is assumed that the second frequency of the second ultrasonic vibration is a triple higher-order frequency of the first frequency. Note that in FIG. 2, the vibration velocity is indicated in a direction perpendicular to the longitudinal axis L, but this is merely schematic illustration, and the actual direction of vibration is along the longitudinal axis L.

Referring to the upper part of FIG. 2, the configuration of the probe 11 will be described.

The probe 11 is formed of, for example, a titanium alloy such as Ti-6Al-4V.

The probe 11 extends along the longitudinal axis L which is defined by a proximal end A1 and a distal end A2 on a side opposite to the proximal end A1. The transducer 12 is connected to the proximal end A1.

The probe 11 is formed in an elongated hollow cylindrical shape or solid rod shape extending along the longitudinal axis L. The length of the probe 11 is set to be a half-wave length based on the first frequency. Note that the length of the probe 11 may be set to an integral multiple of the half-wave length based on the first frequency.

The probe 11 includes a first extension portion 111, a first outside-diameter variation portion 112, a second extension portion 113, a second outside-diameter variation portion 114 and a third extension portion 115. The probe 11 may be formed integral, or may be formed of separate members. The probe 11 may be formed of two or more members.

The first extension portion 111 has a shape extending along the longitudinal axis L. The first extension portion 111 has, for example, a columnar shape with a uniform outside diameter. The first extension portion 111 includes, on the proximal end A1 side, a proximal end surface B1 which is perpendicular to the longitudinal axis L. The transducer 12 is connected to the proximal end surface B1. The first extension portion 111 includes, on the distal end A2 side, a first boundary surface B2 which is perpendicular to the longitudinal axis L. The first boundary surface B2 is a surface which is a boundary between the first extension portion 111 and the first outside-diameter variation portion 112. Note that when the first extension portion 111 and the first outside-diameter variation portion 112 are integrally formed, the first boundary surface B2 is an imaginary plane. The proximal end surface B1 and first boundary surface B2 are circular surfaces. The outside diameter of the proximal end surface B1 is equal to the outside diameter of the first boundary surface B2 in FIG. 2, but these may be different. The outside diameter of the first boundary surface B2 is referred to as "first outside diameter d11".

The first outside-diameter variation portion 112 has a truncated conical shape having a gradually decreasing outside diameter from the proximal end A1 side toward the distal end A2 side. The length of the first outside-diameter variation portion 112 along the longitudinal axis L is referred to as "first length L1". The first outside-diameter variation portion 112 includes the above-described first boundary surface B2 on the proximal end A1 side. The first outside-diameter variation portion 112 includes, on the distal end A2 side, a second boundary surface B3 which is perpendicular to the longitudinal axis L. The second boundary surface B3 is a surface which is a boundary between the first outside-diameter variation portion 112 and the second extension portion 113. Note that when the first outside-diameter variation portion 112 and the second extension portion 113 are integrally formed, the second boundary surface B3 is an imaginary plane. The second boundary surface B3 is a circular surface. The outside diameter of the second boundary surface B3 is referred to as "second outside diameter d12". The diameter d12 is less than d11.

The first outside-diameter variation portion 112 increases the velocity of the first ultrasonic vibration and/or second ultrasonic vibration. An increase rate of vibration velocity (and energy proportional to vibration velocity) by the first outside-diameter variation portion 112 will be described later.

The second extension portion 113 has a shape extending along the longitudinal axis L. The second extension portion 113 has, for example, a columnar shape with a uniform outside diameter. The second extension portion 113 includes the above-described second boundary surface B3 on the proximal end A1 side. The second extension portion 113 includes, on the distal end A2 side, a third boundary surface B4 which is perpendicular to the longitudinal axis L. The third boundary surface B4 is a surface which is a boundary between the second extension portion 113 and the second outside-diameter variation portion 114. Note that when the second extension portion 113 and the second outside-diameter variation portion 114 are integrally formed, the third boundary surface B4 is an imaginary plane. The third boundary surface B4 is a circular surface. The outside diameter of the third boundary surface B4 is equal to the outside diameter of the third boundary surface B4 in FIG. 2, but these may be different. The outside diameter of the third boundary surface B4 is referred to as "third outside diameter d21".

The second outside-diameter variation portion 114 is located on the distal end A2 side with respect to the first outside-diameter variation portion 112. The second outside-diameter variation portion 114 has a truncated conical shape having a gradually decreasing outside diameter from the proximal end A1 side toward the distal end A2 side. The length of the second outside-diameter variation portion 114 along the longitudinal axis L is referred to as "second length L2". The second outside-diameter variation portion 114 includes the above-described third boundary surface B4 on the proximal end A1 side. The second outside-diameter variation portion 114 includes, on the distal end A2 side, a fourth boundary surface B5 which is perpendicular to the longitudinal axis L. The fourth boundary surface B5 is a surface which is a boundary between the second outside-diameter variation portion 114 and the third extension portion 115. Note that when the second outside-diameter variation portion 114 and the third extension portion 115 are integrally formed, the fifth boundary surface B5 is an imaginary plane. The fourth boundary surface B5 is a circular surface. The outside diameter of the fourth boundary surface B5 is referred to as "fourth diameter d22". The diameter d22 is less than d21.

The second outside-diameter variation portion 114 increases the velocity of the first ultrasonic vibration and/or second ultrasonic vibration. An increase rate of vibration velocity (and energy proportional to vibration velocity) by the second outside-diameter variation portion 114 will be described later.

The second outside-diameter variation portion 114 includes a flange 1141. The flange 1141 may be formed integral with, or separate from, the second outside-diameter variation portion 114. The position of the flange 1141 in the second outside-diameter variation portion 114 and the function of the flange 1141 will be described later.

The third extension portion 115 has a shape extending along the longitudinal axis L. The third extension portion 115 has, for example, a columnar shape with a uniform outside diameter. The third extension portion 115 includes the above-described fourth boundary surface B5 on the proximal end A1 side. The third extension portion 115 includes, on the distal end A2 side, a distal end surface B6 which is perpendicular to the longitudinal axis L. The distal end surface B6 is a circular surface. The outside diameter of the distal end surface B6 is equal to the outside diameter of the first boundary surface B2 in FIG. 2, but these may be different.

The third extension portion 115 includes the treatment section 1151 near the distal end A2. The treatment section 1151 comes in contact with a cartilage and/or a cortical bone, which is a treated target in an articulation. The treatment section 1151 treats a subject by performing ultrasonic vibration. The treatment section 1151 may be processed to have such a shape as to be capable of abrading a treated target.

Referring to the lower part of FIG. 2, a description is given of the first ultrasonic vibration and second ultrasonic vibration which are transmitted in the probe 11.

The first ultrasonic vibration (solid line) is a standing wave. The first ultrasonic vibration has anti-nodes, which move forward and backward along the longitudinal axis L, at positions of the proximal end A1 and distal end A2 of the probe 11. The first ultrasonic vibration has one node between the proximal end. Al and distal end A2 of the probe 11.

The second ultrasonic vibration (broken line) is a standing wave. The second ultrasonic vibration has anti-nodes, which move forward and backward along the longitudinal axis L, at positions of the proximal end A1 and distal end A2 of the probe 11. The second ultrasonic vibration has three nodes between the proximal end A1 and distal end A2 of the probe 11. Of the three nodes, the node located most on the proximal end A1 side is referred to as "first node". The node, which is located on the distal end A2 side with respect to the first node, is referred to as "second node". The node, which is located on the distal end A2 side with respect to the second node, is referred to as "third node". The positions of the first node and third node of the second ultrasonic vibration do not coincide with the position of the node of the first ultrasonic vibration. On the other hand, the position of the second node of the second ultrasonic vibration coincides with the position of the node of the first ultrasonic vibration. The position of the second node of the second ultrasonic vibration, which coincides with the position of the node of the first ultrasonic vibration, is referred to as "position of the common node". Note that if the second frequency is an odd number of times the first frequency, a common node exists in the probe 11.

Referring to FIG. 2, a description is given of the positions of the first outside-diameter variation portion 112 and second outside-diameter variation portion 114 in the probe 11.

The probe 11 includes the first outside-diameter variation portion 112 at the position of the first node of the second ultrasonic vibration. As illustrated in FIG. 2, the probe 11 includes the first outside-diameter variation portion 112, for example, such that the position of the first boundary surface B2 coincides with the position of the first node of the second ultrasonic vibration.

The probe 11 includes the second outside-diameter variation portion 114 at the position of the common node. As illustrated in FIG. 2, the probe 11 includes the second outside-diameter variation portion 114, for example, such that the position of the third boundary surface B4 coincides with the position of the common node.

The flange 1141 is located at the position of the third boundary surface B4 which is the position of the common node. The flange 1141 fixes the probe 11 to a casing (not shown). The flange 1141 prevents the probe 11 from vibrating in a direction perpendicular to the longitudinal axis L. The position of the common node is a position at which the velocities of the first ultrasonic vibration and second ultrasonic vibration become zero. Thus, the flange 1141 does not hinder the first ultrasonic vibration and second ultrasonic vibration which are transmitted to the distal end A2 of the probe 11.

The configurations of the first outside-diameter variation portion 112 and second outside-diameter variation portion 114 will now be described.

An increase rate of vibration velocity by the first outside-diameter variation portion 112 in the first mode is referred to as "first increase rate". An increase rate of vibration velocity by the second outside-diameter variation portion 114 in the first mode is referred to as "second increase rate". A product of the first increase rate and second increase rate is referred to as "first total increase rate". An increase rate of vibration velocity by the first outside-diameter variation portion 112 in the second mode is referred to as "third increase rate". An increase rate of vibration velocity by the second outside-diameter variation portion 114 in the second mode is referred to as "fourth increase rate". A product of the third increase rate and fourth increase rate is referred to as "second total increase rate".

The first increase rate and third increase rate vary depending on the first frequency, second frequency, the material of the first outside-diameter variation portion 112, first length L1, first outside diameter d11, second outside diameter d12, etc. The second increase rate and fourth increase rate vary depending on the first frequency, second frequency, the material of the second outside-diameter variation portion 114, second length L2, third outside diameter d21, fourth outside diameter d22, etc.

The first outside-diameter variation portion 112 and second outside-diameter variation portion 114 are properly configured such that the first total increase rate coincides with the second total increase rate.

The functions of the first outside-diameter variation portion 112 and second outside-diameter variation portion 114 will now be described.

Since the first outside-diameter variation portion 112 is located at the position of the first node of the second ultrasonic vibration, the first outside-diameter variation portion 112 increases the velocity of the second ultrasonic vibration. On the other hand, the first outside-diameter variation portion 112 hardly contributes to an increase of the first ultrasonic vibration. The reason for this is that the node of the first ultrasonic vibration is located at a position remote from the first outside-diameter variation portion 112. Thus, the first increase rate is substantially 1 time.

In this manner, the first outside-diameter variation portion 112 selectively increases the velocity of the second ultrasonic vibration from between the velocity of the first ultrasonic vibration and the velocity of the second ultrasonic vibration.

The second outside-diameter variation portion 114 is located at the position of the common node of the first ultrasonic vibration and second ultrasonic vibration. Thus, the second outside-diameter variation portion 114 increases both the velocity of the first ultrasonic vibration and the velocity of the second ultrasonic vibration.

However, the second increase rate and fourth increase rate by the second outside-diameter variation portion 114 are different for the following reason. The second increase rate and fourth increase rate relate to the length L2 of the second outside-diameter variation portion 114 in relation to the wavelength. The ratio of the length L2 of the second outside-diameter variation portion 114 to the wavelength is higher in the second mode than in the first mode. Specifically, the variation of the outside diameter of the second outside-diameter variation portion 114 in relation to the wavelength is gentler in the second mode than in the first mode. Thus, the fourth increase rate is less than the second increase rate.

In the first mode, the probe 11 vibrates at the first frequency and a first amplitude. In the first mode, the probe 11 generates at the distal end A2 a first vibration velocity which is a product of the first frequency and the first amplitude at the distal end A2. In the second mode, the probe 11 vibrates at the second frequency and a second amplitude which is less than the first amplitude. In the second mode, the probe 11 generates at the distal end A2 a second vibration velocity which is a product of the second frequency and the second amplitude at the distal end A2 which is less than the first amplitude. By the functions of the first outside-diameter variation portion 112 and second outside-diameter variation portion 114, the second vibration velocity in the second mode coincides or substantially coincides with the first vibration velocity in the first mode. In proportion to the vibration velocity at the distal end A2 of the probe 11, the frictional heat energy $W_\mu$ coincides or substantially coincides between the first mode and second mode.

As described above, the functions of the first outside-diameter variation portion 112 and second outside-diameter variation portion 114 are different from each other. Thus, the first outside-diameter variation portion 112 can properly be configured in accordance with the configuration of the second outside-diameter variation portion 114, so that the first total increase rate coincides with the second total increase rate. Here, an example is described in which the first outside-diameter variation portion 112 is configured in accordance with the configuration of the second outside-diameter variation portion 114. Although a description is omitted here, the second outside-diameter variation portion 114 can similarly be configured in accordance with the configuration of the first outside-diameter variation portion 112.

The first outside-diameter variation portion 112 and second outside-diameter variation portion 114 are configured such that the first total increase rate coincides with the second total increase rate. Thus, the following equation (2) is established.

(third increase rate)/(first increase rate)=(second increase rate)/(fourth increase rate)   equation (2)

Note that the sign "=" used in the present embodiment is intended to mean "coincide or substantially coincide".

As described above, the first increase rate is substantially 1 time. The equation (2) can be expressed as the following equation (3).

(third increase rate)=(second increase rate)/(fourth increase rate)   equation (3)

The first outside-diameter variation portion 112 can be configured so as to satisfy the equation (3).

Further, in order to make the first total increase rate and second total increase rate coincide, it is preferable that the outside diameter of the first outside-diameter variation portion 112 varies more gently than the outside diameter of the second outside-diameter variation portion 114. Thus, the first outside-diameter variation portion 112 is configured so as to satisfy at least one of the following equation (4) and equation (5).

(first outside diameter $d11$)/(second outside diameter $d12$)<(third outside diameter $d21$)/(fourth outside diameter $d22$)   equation (4)

(first length $L1$)>(second length $L2$)   equation (5)

Concrete examples of the increase rates by the first outside-diameter variation portion 112 and second outside-diameter variation portion 114 will be described.

Here, the following conditions are used. The probe 11 is formed of Ti-6Al-4V. The first mode is a basic mode in which the first frequency is 47 kHz. The second mode is a triple higher-order mode in which the second frequency is a triple higher-order frequency of the first frequency. The parameters of the second outside-diameter variation portion 114 are set as follows. The third outside diameter d21 is 5 mm. The fourth outside diameter d22 is 3 mm. The second length L2 is 10 mm.

FIG. 3 is a table illustrating increase rates by the first outside-diameter variation portion 112 and second outside-diameter variation portion 114.

The increase rate by the second outside-diameter variation portion 114 is described. The increase rate of vibration velocity by the second outside-diameter variation portion 114 is calculated based on the above-described conditions. The second increase rate is 5.83 times. The fourth increase rate is 3.25 times. It is understood that the fourth increase rate is less than the second increase rate.

The increase rate by the first outside-diameter variation portion 112 is described. As described above, the first increase rate is substantially 1 time. The third increase rate is calculated as 1.79 times by referring to the equation (3).

The first total increase rate is substantially 5.83 times, and the second total increase rate is 5.83 times. Thus, by configuring the first outside-diameter variation portion 112 to have the third increase rate of 1.79 times, the first total increase rate and second total increase rate coincide.

The advantageous effects of the first mode and second mode will be described.

As described above, in proportion to the vibration velocity at the distal end A2 of the probe 11, the frictional heat energy $W_\mu$ coincides between the first mode and second mode. In order that the frictional heat energy $W_\mu$ coincides between the first mode and second mode, the magnitude of amplitude varies since the frequency is determined in each mode. Specifically, since the ultrasonic vibration of the first mode is vibration of a lower frequency than the ultrasonic vibration of the second mode, the amplitude of the ultrasonic vibration of the first mode is greater than the amplitude of the ultrasonic vibration of the second mode.

In the first mode, the amplitude at the distal end A2 of the probe 11 is greater than the amplitude at the distal end A2 of the probe 11 in the second mode. Thus, the treatment instrument 1 causes in the treatment section 1151 an enough and proper hammering effect to abrade the cortical bone which is the treated target in the articulation. The surgeon can abrade the cortical bone which is the treated target in the articulation, by using the treatment instrument 1 in which the first mode is set. In addition, the treatment instrument 1 not only causes the hammering effect in the treatment section 1151, but also causes frictional heat between the treatment section 1151 and the tissue which is in contact with the treatment section 1151. Thus, in the first mode, the treatment instrument 1 can also abrade (dissolve) the cartilage.

In the second mode, the frictional heat energy $W_\mu$ coincides with the frictional heat energy $W_\mu$ in the first mode. Thus, the function of abrasion by the frictional heat in the second mode is not different from the function of abrasion by the frictional heat in the first mode. The treatment instrument 1 causes enough and proper frictional heat to abrade the cartilage, which is the treated target in the articulation, between the treatment section 1151 and the cartilage which is in contact with the treatment section 1151.

The surgeon can abrade the cartilage which is the treated target in the articulation, by using the treatment instrument 1 in which the second mode is set. The time required for abrading the cartilage by the treatment instrument 1, in which the second mode is set, does not become longer than the time required for abrading the cartilage by the treatment instrument 1 in which the first mode is set.

Moreover, in the second mode, the amplitude at the distal end A2 of the probe 11 is less than the amplitude at the distal end A2 of the probe 11 in the first mode. Thus, the hammering effect in the treatment section 1151 becomes lower than the hammering effect in the treatment section 1151 in the first mode. When the surgeon abrades the cartilage which is the treated target in the articulation, by using the treatment instrument 1 in which the second mode is set, it becomes more difficult than in the first mode to abrade the cortical bone which is near the cartilage and is not the treated target.

In this manner, in the second mode, the function of abrasion by frictional heat becomes dominant over the function of abrasion by the hammering effect.

According to the present embodiment, the treatment instrument 1 and treatment system 100 can operate, in accordance with the treated target, either in the first mode with the function of a sufficient hammering effect, or in the second mode in which the function of abrasion by the frictional heat is dominant over the function of the hammering effect.

Modifications of the present embodiment will now be described.

Figure 4:
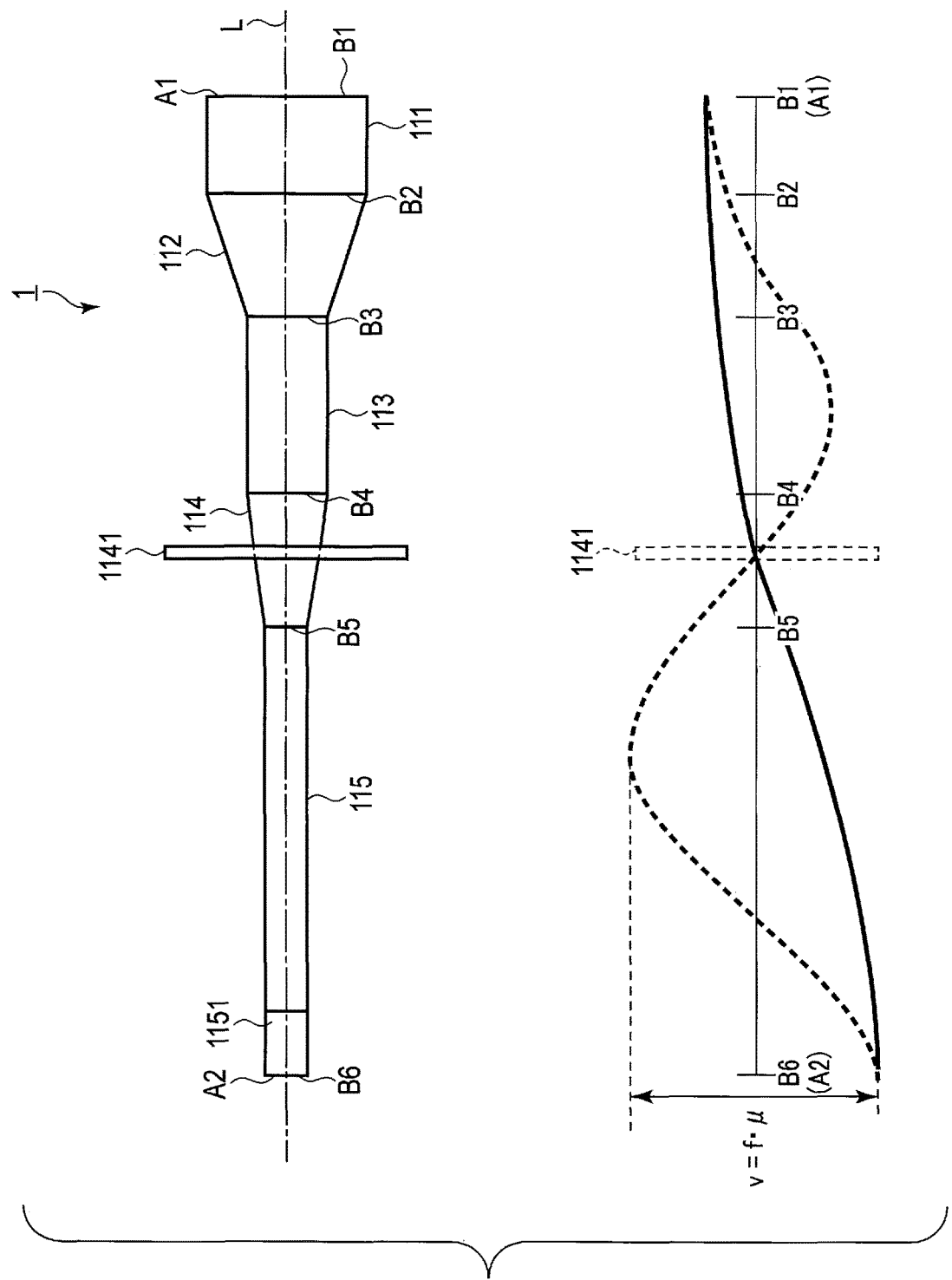
FIG. 4 is a schematic view illustrating a modification of the ultrasonic treatment instrument for articulations according to an embodiment.

FIG. 4 is a schematic view illustrating a modification of the treatment instrument 1 according to the present embodiment.

An upper part of FIG. 4 is a schematic view illustrating an example of the probe 11. A lower part of FIG. 4 is a schematic view illustrating vibration velocity (solid line) of first ultrasonic vibration and vibration velocity (broken line) of second ultrasonic vibration, which are transmitted in the probe 11. The probe 11 illustrated in FIG. 4 differs from the probe 11 illustrated in FIG. 2 with respect to positions where the probe 11 includes the first outside-diameter variation portion 112 and second outside-diameter variation portion 114.

The probe 11 may include the first outside-diameter variation portion 112 such that the position of the first node of the second ultrasonic vibration is located on the distal end A2 side with respect to the first boundary surface B2 and is located on the proximal end A1 side with respect to the second boundary surface B3.

The probe 11 may include the second outside-diameter variation portion 114 such that the position of the common node is located on the distal end A2 side with respect to the third boundary surface B4 and is located on the proximal end A1 side with respect to the fourth boundary surface B5.

The second outside-diameter variation portion 114 includes the flange 1141 at the position of the common node.

In another modification, the probe 11 may include three or more outside-diameter variation portions. For example, the probe 11 may include outside-diameter variation portions at respective positions of a plurality of nodes of the second ultrasonic vibration, aside from the position of the common node. The condition in this case is that the vibration velocity at the distal end A2 of the probe 11 coincides or substantially coincides between the first mode and second mode.

In another modification, the transducer 12 may be configured like the above-described probe 11. Thereby, the increase rate of vibration velocity by the transducer 12 is improved. Note that when the increase rate of vibration velocity by the transducer 12 is set to be 1 time, the transducer 12 does not need to have the same configuration as the probe 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment system for articulations, comprising:
    an ultrasonic treatment instrument; and
    a controller configured to control driving of an ultrasonic treatment instrument for articulations,
    the controller including:
    a bone abrasion mode in which vibration is performed at a first predetermined frequency and a first predetermined amplitude; and
    a cartilage dissolution mode in which vibration is performed at a second predetermined frequency which is higher than the first predetermined frequency, and a second predetermined amplitude which is less than the first predetermined amplitude,
    wherein the ultrasonic treatment instrument includes a vibration transmission member extending along a longitudinal axis defined by a proximal end and a distal end on a side opposite to the proximal end, and configured to transmit first ultrasonic vibration in the bone abrasion mode, and to transmit second ultrasonic vibration in the cartilage dissolution mode,
    wherein the vibration transmission member includes a first outside-diameter variation portion having a gradually decreasing outside diameter from the proximal end side toward the distal end side and configured to increase a velocity of the first ultrasonic vibration and/or the second ultrasonic vibration, and a second outside-diameter variation portion having a gradually decreasing outside diameter from the proximal end side toward the distal end side, on the distal end side with respect to the first outside-diameter variation portion, and configured to increase the velocity of the first ultrasonic vibration and/or the second ultrasonic vibration.

2. The ultrasonic treatment system for articulations of claim 1, wherein the second predetermined frequency is an odd number of times the first predetermined frequency.

3. The ultrasonic treatment system for articulations of claim 1, wherein a first vibration velocity, which is a product of the first predetermined frequency and the first predetermined amplitude, and a second vibration velocity, which is a product of the second predetermined frequency and the second predetermined amplitude, coincide or substantially coincide.

4. The ultrasonic treatment system for articulations of claim 1, wherein the bone abrasion mode is a mode for treating a cortical bone and a cancellous bone, and
    the cartilage dissolution mode is a mode for treating a cartilage.

5. An ultrasonic treatment instrument for articulations, comprising:
    a bone abrasion mode in which vibration is performed at a first predetermined frequency and a first predetermined amplitude; and
    a cartilage dissolution mode in which vibration is performed at a second predetermined frequency which is higher than the first predetermined frequency, and a second predetermined amplitude which is less than the first predetermined amplitude,
    wherein the ultrasonic treatment instrument further includes a vibration transmission member extending along a longitudinal axis defined by a proximal end and a distal end on a side opposite to the proximal end, and configured to transmit first ultrasonic vibration in the bone abrasion mode, and to transmit second ultrasonic vibration in the cartilage dissolution mode,
    wherein the vibration transmission member includes a first outside-diameter variation portion having a gradually decreasing outside diameter from the proximal end side toward the distal end side and configured to increase a velocity of the first ultrasonic vibration and/or the second ultrasonic vibration, and a second outside-diameter variation portion having a gradually decreasing outside diameter from the proximal end side toward the distal end side, on the distal end side with respect to the first outside-diameter variation portion, and configured to increase the velocity of the first ultrasonic vibration and/or the second ultrasonic vibration.

6. The ultrasonic treatment instrument for articulations of claim 5, wherein the second predetermined frequency is an odd number of times the first predetermined frequency.

7. The ultrasonic treatment instrument for articulations of claim 5, wherein a first vibration velocity, which is a product of the first predetermined frequency and the first predetermined amplitude, and a second vibration velocity, which is a product of the second predetermined frequency and the second predetermined amplitude, coincide or substantially coincide.

8. The ultrasonic treatment instrument for articulations of claim 5, wherein the bone abrasion mode is a mode for treating a cortical bone and a cancellous bone, and
    the cartilage dissolution mode is a mode for treating a cartilage.

9. The ultrasonic treatment instrument for articulations of claim 5, wherein the vibration transmission member includes the first outside-diameter variation portion at a position of a first node of the second ultrasonic vibration, and includes the second outside-diameter variation portion at a position of a second node of the second ultrasonic vibration, the position of the second node coinciding with a position of a node of the first ultrasonic vibration.

10. The ultrasonic treatment instrument for articulations of claim 5, wherein the second outside-diameter variation portion includes a flange at the position of the second node.

11. The ultrasonic treatment instrument for articulations of claim 5, wherein the first outside-diameter variation portion is configured such that an increase rate of a vibration velocity by the first outside-diameter variation portion in the cartilage dissolution mode coincides or substantially coincides with a value calculated by dividing an increase rate of a vibration velocity by the second outside-diameter variation portion in the bone abrasion mode by an increase rate of a vibration velocity by the second outside-diameter variation portion in the cartilage dissolution mode.

12. The ultrasonic treatment instrument for articulations of claim 5, wherein when an outside diameter of a surface perpendicular to the longitudinal axis on the proximal end side in the first outside-diameter variation portion is set as a first diameter, an outside diameter of a surface perpendicular to the longitudinal axis on the distal end side in the first outside-diameter variation portion is set as a second diameter, an outside diameter of a surface perpendicular to the longitudinal axis on the proximal end side in the second outside-diameter variation portion is set as a third diameter, an outside diameter of a surface perpendicular to the longitudinal axis on the distal end side in the second outside-diameter variation portion is set as a fourth diameter, a length of the first outside-diameter variation portion along the longitudinal axis is set as a first length, and a length of the second outside-diameter variation portion along the longitudinal axis is set as a second length, the first outside-diameter variation portion is configured to satisfy at least one of:

(the first outside diameter)/(the second outside diameter) <(the third outside diameter)/(the fourth outside diameter), and (the first length)>(the second length).

13. An ultrasonic treatment system for articulations, comprising:

an ultrasonic treatment instrument; and means for controlling driving of the ultrasonic treatment instrument for articulations, the means for controlling including:

a bone abrasion mode in which vibration is performed at a first predetermined frequency and a first predetermined amplitude; and a cartilage dissolution mode in which vibration is performed at a second predetermined frequency which is higher than the first predetermined frequency, and a second predetermined amplitude which is less than the first predetermined amplitude, wherein the means for ultrasonic treatment further includes a vibration transmission means extending along a longitudinal axis defined by a proximal end and a distal end on a side opposite to the proximal end, and configured to transmit first ultrasonic vibration in the bone abrasion mode, and to transmit second ultrasonic vibration in the cartilage dissolution mode, wherein the vibration transmission means includes a first outside-diameter variation portion having a gradually decreasing outside diameter from the proximal end side toward the distal end side and configured to increase a velocity of the first ultrasonic vibration and/or the second ultrasonic vibration, and a second outside-diameter variation portion having a gradually decreasing outside diameter from the proximal end side toward the distal end side, on the distal end side with respect to the first outside-diameter variation portion, and configured to increase the velocity of the first ultrasonic vibration and/or the second ultrasonic vibration.

14. An operation method of an ultrasonic treatment system for articulations, comprising:

controlling driving of an ultrasonic treatment instrument for articulations, the controlling including:

a bone abrasion mode in which vibration is performed at a first predetermined frequency and a first predetermined amplitude; and a cartilage dissolution mode in which vibration is performed at a second predetermined frequency which is higher than the first predetermined frequency, and a second predetermined amplitude which is less than the first predetermined amplitude, wherein the controlling driving includes transmitting a first ultrasonic vibration in the bone abrasion mode, and transmitting a second ultrasonic vibration in the cartilage dissolution mode, the transmitting occurring using a vibration transmission member that extends along a longitudinal axis defined by a proximal end and a distal end on a side opposite to the proximal end, and wherein the controlling driving also includes increasing a velocity of the first ultrasonic vibration and/or the second ultrasonic vibration, the increasing the velocity occurring using a first outside-diameter variation portion having a gradually decreasing outside diameter from the proximal end side toward the distal end side, and a second outside-diameter variation portion having a gradually decreasing outside diameter from the proximal end side toward the distal end side, on the distal end side with respect to the first outside-diameter variation portion.

15. The ultrasonic treatment system for articulations of claim 1, further comprising a signal generator configured to generate a signal for cartilage treatment and a signal for bone treatment, wherein the controller is configured to control the driving of the ultrasonic treatment instrument for articulations in response to the signal for cartilage treatment of the signal for bone treatment.

* * * * *